United States Patent [19]

Ho Chang et al.

[11] 4,029,583

[45] June 14, 1977

[54] CHROMATOGRAPHIC SUPPORTS AND METHODS AND APPARATUS FOR PREPARING THE SAME

[75] Inventors: Shung Ho Chang; Frederick E. Regnier, both of West Lafayette, Ind.

[73] Assignee: Purdue Research Foundation, West Lafayette, Ind.

[22] Filed: Feb. 28, 1975

[21] Appl. No.: 554,071

[52] U.S. Cl. .................... 210/502; 55/386; 210/198 C
[51] Int. Cl.$^2$ ................ B01D 39/00; B01D 39/14
[58] Field of Search .............. 210/24 C, 36, 31 C, 210/198 C, 502; 55/67, 386

[56] References Cited

UNITED STATES PATENTS

| | | | |
|---|---|---|---|
| 3,263,401 | 8/1966 | Supina | 55/67 |
| 3,500,616 | 3/1970 | Boosart | 55/386 |
| 3,514,925 | 6/1970 | Bossart | 55/386 |
| 3,586,626 | 6/1971 | Heitz et al. | 210/24 C |
| 3,657,117 | 4/1972 | Pfitzner | 210/24 C |
| 3,660,966 | 5/1972 | Finch et al. | 55/67 |
| 3,664,967 | 5/1972 | Stehl | 210/24 C |
| 3,722,181 | 3/1973 | Kirkland | 210/24 C |
| 3,795,313 | 3/1974 | Kirkland et al. | 210/198 C |
| 3,808,125 | 4/1974 | Good | 210/198 C |
| 3,878,092 | 4/1975 | Fuller | 210/198 C |

OTHER PUBLICATIONS

Chem. Abs.; vol. 81; p. 245; Article No. 16999r.
Chem. Abs.; vol. 81; p. 409; Article No. 111702x.
Chem. Abs.; vol. 82; p. 300; Article No. 160630b.

*Primary Examiner*—Frank W. Lutter
*Assistant Examiner*—Frank Sever
*Attorney, Agent, or Firm*—John R. Nesbitt

[57] ABSTRACT

Chromatographic supports are disclosed as are methods and apparatus for preparing the same. The support includes an inorganic support matrix that is capable of reacting with silanols, a stationary phase, and an intermediate silane coupling agent having a silicon functional group capable of bonding to the support surface and an organic functional group capable of bonding to the stationary phase. The inorganic support matrix is preferably controlled porosity glass or silica while the coupling agent may include a simple carbohydrate, a carbohydrate derivative, or a polymer to which the stationary phase is attached. A plurality of chromatographic supports and stationary phases are disclosed and two methods of bonding of stationary phases to supports are also disclosed. In addition, apparatus including a fluidized bed is also disclosed to prepare supports.

3 Claims, 10 Drawing Figures

CHROMATOGRAPHIC SUPPORTS AND METHODS AND APPARATUS FOR PREPARING THE SAME

FIELD OF THE INVENTION

This invention relates to chromotographic supports, and, more particularly, relates to chromotographic supports having a silane coupling agent bonding a stationary phase to an inorganic support material, as well as methods and apparatus for preparing such supports.

BACKGROUND OF THE INVENTION

Resolution of components in a chromatographic system is achieved by partitioning solutes between two physcially distinct phases that share a common interfacial boundary. These two phases which are designated the "stationary phase" ($P_s$) and the "mobile phase" ($P_m$) are arranged in a narrow channel along the flow axis of the mobile phase and are the heart of the separation system. It may be shown that the distribution of solute molecules between these phases is a constant K usually referred to as the partition coefficient. The partition coefficient for a solute is expressed mathematically as $K = C_s/C_m$, where $C_s$ is the concentration of solute per unit volume of stationary phase and $C_m$ is the concentration of solute per unit volume of mobile phase. It has been shown experimentally that if the K values for two compounds are sufficiently different, resolution will be achieved during passage through the chromatographic system. Maximum resolution is achieved by choosing the two phases that produce the greatest difference in the partition coefficients of solutes.

The stationary phase in the case of ion exchange and hydrophobic chromatography is immobilized on a support matrix. The basis for partitioning in ion exchange chromatography is ionic association of solutes with an anionic or cationic stationary phase bonded to an inert support. On the other hand, hydrophobic stationary phases also show an affinity for many biological molecules. Differential binding of solutes to hydrophobic supports is based on the relative hydrophobicity of solutes.

Carbohydrates have been used extensively as the inert support matrix to which stationary phases are immobilized for the chromatography of proteins, nucleic acids, polysaccharides, lipoproteins, peptides, hormones, and vitamins. Since they are hydrophilic, water causes carbohydrates to swell into a porous matrix into which biological macromolecules may penetrate and be partitioned. The success of carbohydrates as chromatographic supports is based primarily upon: the ability of the carbohydrate to imbibe large quantities of water and swell into a hydrophilic matrix; the chemical stability of the formed hydrophilic matrix and the ease with which it is derivatized with ion exchange groups; and the ability of carbohydrates to stabilize sensitive biological compounds.

The primary disadvantage of the carbohydrate chromatography supports is that the hydrophilic matrix is sensitive to changes in pH, ionic strength, and pressure. Changes in any of these parameters can cause contraction of the matrix and losses in chromatographic efficiency. This problem is particularly acute in high speed analysis where it is desirable to use forced flow and large changes in pH and ionic strength during the development of columns. Operation of carbohydrate columns under such a protocol results in collapse of the support and complete loss of chromatographic efficiency.

High speed analysis at high $P_m$ flow rates and pressures are currently carried out on rigid inorganic supports. Modern high speed chromatography supports are capable of withstanding both pressures and flow rates 100 times greater than carbohydrate columns. It has not been possible, however, to separate many biological compounds (proteins, nucleic acids, and peptides) on these supports due to adsorption and/or denaturation. Hence high porosity glass, for example, must have both internal and external surfaces coated to accomplish the desired end.

This invention seeks to overcome the disadvantages of both inorganic and carbohydrate supports by forming a composite of the two. These supports have the mechanical ability of inorganic supports and the separation characteristics of carbohydrates.

It has heretofore been known that a bonded support can be produced by covalently linking a layer of carbohydrate material to an inorganic support, and this is shown in copending U.S. Patent Applications, Ser. Nos. 447,640 and 537,197, filed Mar. 4, 1974 and Dec. 30, 1974, respectively, by Frederick E. Regnier, entitled "Bonded Carbohydrate Stationary Phases For Chromatography" and assigned to the assignee of the present invention. U.S. Patent Application Ser. No. 447,640 is now abandoned and U.S. Patent Application Ser. No. 537,197 issued on Sept. 28, 1976 as U.S. Pat. No. 3,983,299.

It has also heretofore been known that a polymer might be used in chromatographic apparatus, but such use has been as the stationary phase rather than as a stabilizing or coupling agent. See, for example, U.S. Pat. No. 3,808,125 issued to Robert G. Good on Apr. 30, 1974.

SUMMARY OF THE INVENTION

This invention provides chromatographic supports that are useful in high speed chromatographic analysis of biological macromolecules by hydrophobic and ion exchange partitioning. A plurality of supports are provided that have the following essential features: 1) sufficient mechanical stability to withstand high mobile phase velocities and pressure; 2) enough porosity to allow penetration and partitioning of biological macromolecules into the support; 3) sufficient hydrolytic stability of bonded stationary phases to allow extended operation in aqueous systems; and 4) partitioning capacities equivalent to those of classical supports. Methods and apparatus for preparing such supports are also provided.

In essence, an intermediate silane coupling agent is provided that has a silicon functional group capable of bonding to the surface of a support and an organic functional group capable of bonding to a stationary phase wherein the organic functional group may include a polymer to which the stationary phase is attached.

It is therefore an object of this invention to provide an improved chromatographic support.

It is another object of this invention to provide an improved chromatographic support useful in high speed chromatographic analysis of biological macromolecules by hydrophobic and ion exchange partitioning.

It is still another object of this invention to provide an improved chromatographic support that has a silane coupling agent with functional groups one of which bonds to the support and other of which bonds to the stationary phase.

It is yet another object of this invention to provide an improved chromatographic support that has a silane coupling agent one functional group of which includes a polymer for bonding the stationary phase.

It is another object of this invention to provide improved methods for preparing chromatographic supports.

It is yet another object of this invention to provide improved apparatus for preparing chromatographic supports.

It is still another object of this invention to provide an improved chromatographic support useful for chromatography of biological compounds such as proteins, nucleic acids and peptides.

With these and other objects in view which will become apparent to one skilled in the art as the description proceeds, this invention resides in the novel support apparatus and method for forming the same substantially as hereinafter described, and more particularly defined by the appended claims, it being understood that such changes in the precise embodiment of the herein disclosed invention are meant to be included as come within the scope of the claims.

BRIEF DESCRIPTION OF THE DRAWINGS

The accompanying drawings illustrate achieved results and/or apparatus of the invention according to the best mode so far devised for the practical application of the principles thereof, and in which.

DESCRIPTION OF THE INVENTION

Figure 1:
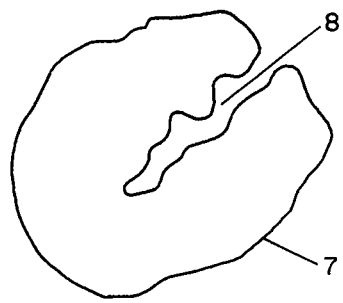
FIG. 1 is a representation of a glass bead with exemplary pore that might be used as the support in this invention.

Chromatographic packings for the ion exchange and hydrophobic chromatography of proteins were prepared by grafting a stationary phase ($P_s$) to a support matrix through silanols. Neither the composition nor dimensions of the inorganic support matrix are important as long as the surface is capable of reacting with silanols. Materials capable of reacting with silanols are glass, porous glass beads, silica gel, porous silica beads, alumina, and diatomaceous earths. Controlled porosity glass and silica are preferred as supports because of their high surface loading capacity, porosity, and availability. The high porosity enables the glass to be coated on both internal and external surfaces.

The coupling of stationary phases ($P_s$) to the surface of supports is achieved through the use of an intermediate silane coupling agent wherein the silicon portion of the molecules is bonded to the support and the organic portion of the molecule is attached to the stationary phase. Structurally the silane coupling agent is an organosilane with a silicon functional group capable of bonding to the support surface and an organic functional group capable of bonding to the stationary phase ($P_s$). The primary function of the coupling agent is to provide a bond between the inorganic support and the stationary phase ($P_s$). This composite has the general chemical formula:

$\equiv SiCH_2CH_2CH_2\text{-}R_1\text{—}P_s$ where $R_1$ (an inert support or coupler) is a simple carbohydrate, derivative, or a polymer and $P_s$ is the stationary phase. In this formula, $-CH_2CH_2CH_2R_1$ couples the stationary phase ($P_s$) to the support. The chemical composition of a series of $R_1$ and $P_s$ groups are shown in Tables I and II respectively, as follows:

TABLE I

| | Formula | $R_1$ Groups | Structural unit(s) |
|---|---|---|---|
| 1. | $-OCH_2\underset{OH}{\overset{|}{C}H}CH_2-$ | | glycerol |
| 2. | $\left[-N\left(CH_2\underset{OH}{\overset{|}{C}H}CH_2\right)_{\!2}\right]_{\!m}\left[-OCH_2CH_2O\right]_{\!n}-$ | | glycerol amine, ethylene glycol |
| 3. | $\left(-OCH_2\underset{OH}{\overset{|}{C}H}CH_2-\right)_{\!m}\left(-OCH_2\underset{\underset{OH}{|}}{\overset{O\diagup}{C}H}CH_2-\right)_{\!n}\left(-OCH_2\underset{\underset{OH}{|}}{\overset{|}{C}H}CH_2-\right)_{\!o}$ | | glycerol, tetrose |
| 4. | $\left(-OCH\underset{OH}{\overset{|}{C}}HCH_2-\right)_{\!m}\left(-OCH_2\overset{O\diagup}{C}HCH_2-\right)_{\!n}-$ | | glycerol |
| 5. | $\left(-OCH_2\overset{O}{\overset{|}{C}}HCH_2-\right)_{\!m}\left(-OCH_2\underset{OH}{\overset{|}{C}}HCH_2-\right)_{\!n}\left(-OCH_2CH_2O-\right)_{\!o}$ | | glycerol, ethylene glycol |

The letters m, n, and o designate the ratio of structural units.

TABLE II

| Formula | P, Groups Chromatographic Function | Structural Unit |
|---|---|---|
| 1. —N(CH$_2$CH$_3$)$_2$ | WAX[a] | diethylamine |
| 2. —OCH$_2$CH$_2$N(CH$_2$CH$_3$)$_2$ | WAX | diethylaminoethanol |
| 3. —OCH$_2$CH$_2$N(CH$_3$)$_2$ | WAX | dimethylaminoethanol |
| 4. $-\text{N}\left(\begin{array}{c}\text{OH}\\|\\\text{CH}_2\text{CHCH}_2\end{array}\right)_2$ | WAX | glycerol amine |
| 5. ⫶NCH$_2$CH$_2$⫶$_n$NH$_2$ | WAX | polyethylene imine |
| 6. —O—CH$_2$CH$_2$N(CH$_3$)$_3$ $^+$ | SAX[b] | choline |
| 7. —OCH$_2$CO$_2$H | WCX[c] | carboxymethyl |
| 8. —OCH$_2$CH$_2$CH$_2$SO$_3$H | SCX[d] | propyl sulfonic acid |
| 9. ⫶OCH$_2$CH$_2$⫶$_n$OH | hydrophobic | polyethylene glycol |
| 10. —O(CH$_2$)$_n$CH$_3$ | hydrophobic | C$_4$—C$_{18}$ alkanol |
| 11. 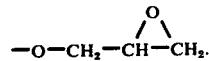 | hydrophobic | phenylethanol |
| 12. —O—⟨⟩—NO$_2$ | hydrophobic | p-nitrophenyl |

[a]WAX designates weak anion exchanger.
[b]SAX signifies strong anion exchanger.
[c]WCX represents weak cation exchanger.
[d]SCX designates strong cation exchanger.

The bonding of stationary phases to supports was achieved in two ways: 1) by bonding the stationary phase directly to an organosilane coupling agent on the surface of the support; or 2) by forming a thin polymer layer on the surface that is attached to the support through the organosilane coupling agent and has the stationary phase bound to the inert polymer matrix. The two organosilane coupling agents used were γ-aminopropyltrimethoxysilane and glycidoxypropyltrimethoxysilane. These monomers have the general formula (CH$_3$O)$_3$SiCH$_2$CH$_2$CH$_2$R$_2$ in which R$_2$ is either —NH or $$-\text{O}-\text{CH}_2-\overset{\overset{\text{O}}{\diagup\diagdown}}{\text{CH}}-\text{CH}_2.$$

In the direct coupling of stationary phases to supports the organosilane, glycidoxypropyltrimethoxysilane was attached to the support according to reaction 1. A 5% aqueous solution of the

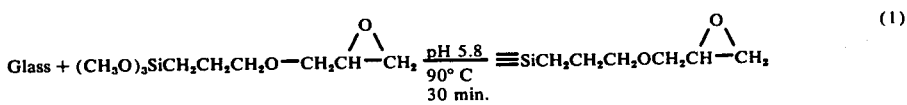  (1)

organosilane monomer adjusted to pH 5.8 was added to the support and heated to 90° C for 30 minutes. After filtration and drying, nucleophilic stationary phases (X) were used to open the oxirane ring and complete the attachment of the stationary phase to the support as indicated in reaction 2.

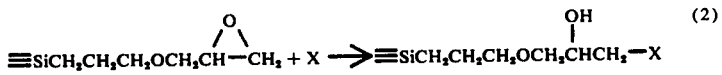  (2)

Exact reaction conditions and catalysts required for addition depend on the chemical nature of X (which can be OH, NH$_2$, HSO$_3$- or HPO$_4$-, for example) and will be further described below.

Synthesis of inert polymeric matrices was achieved by first coating the surface of glycerylpropylsilyl bonded supports with a thin layer of oxirane monomer followed by polymerization. A series of oxirane monomers is shown in Table III as follows:

TABLE III

| Name | Bifunctional Oxirane Monomers Formula |
|---|---|
| Butadiene diepoxide | $\overset{\overset{\text{O}}{\diagup\diagdown}}{\text{CH}_2-\text{CH}}-\overset{\overset{\text{O}}{\diagup\diagdown}}{\text{CH}-\text{CH}_2}$ |
| Diglycidyl ethylene glycol | $\left(\overset{\overset{\text{O}}{\diagup\diagdown}}{\text{CH}_2-\text{CH}}-\text{CH}_2\text{OCH}_2\right)_2$ |
| Diglycidyl butanediol | $\left(\overset{\overset{\text{O}}{\diagup\diagdown}}{\text{CH}_2-\text{CHCH}_2}-\text{OCH}_2\text{CH}_2\right)_2$ |
| Diglycidyl glycerol | $\left(\overset{\overset{\text{O}}{\diagup\diagdown}}{\text{CH}_2-\text{CH}}-\text{CH}_2-\text{O}-\text{CH}_2\right)_2\text{CHOH}$ |

TABLE III-continued

| Name | Bifunctional Oxirane Monomers Formula |
|---|---|
| Triglycidyl glycerol | $\left(\underset{CH_2-CH-CH_2OCH_2}{\overset{O}{\diagdown}}\right)_2 CH-O-CH_2CH\overset{O}{\underset{\diagdown}{-}}CH_2$ |

During the course of polymerization the hydroxyl groups of the glycerylpropylsilyl support become incorporated into the polymer matrix and thus couple the polymer to the support as shown in reactions 3 and 4.

where glass bead 7 has an exemplary pore 8 therein, it being understood that the bead would have a plurality of such pores.

Polymerization is achieved by injecting a volatile polymerization catalyst into the fluidized drying appa-

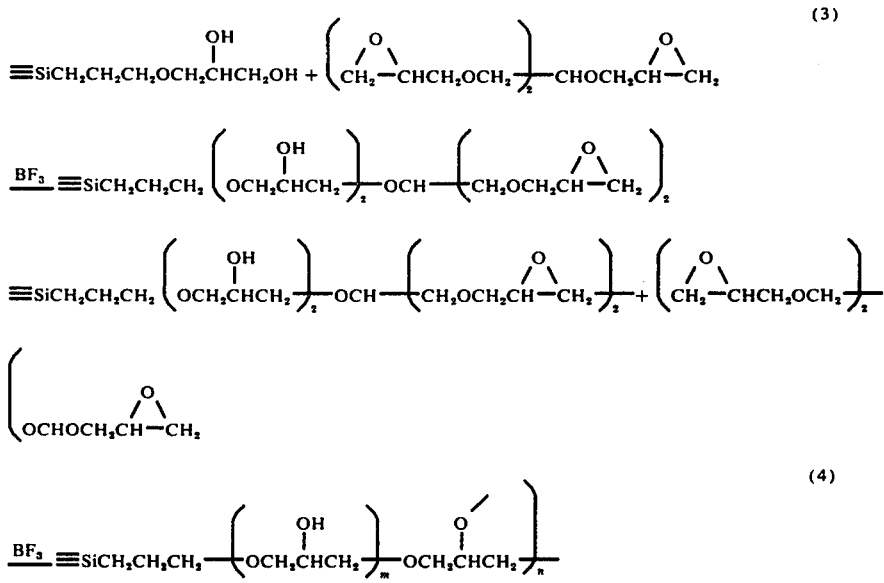

(3)

(4)

Figure 2:
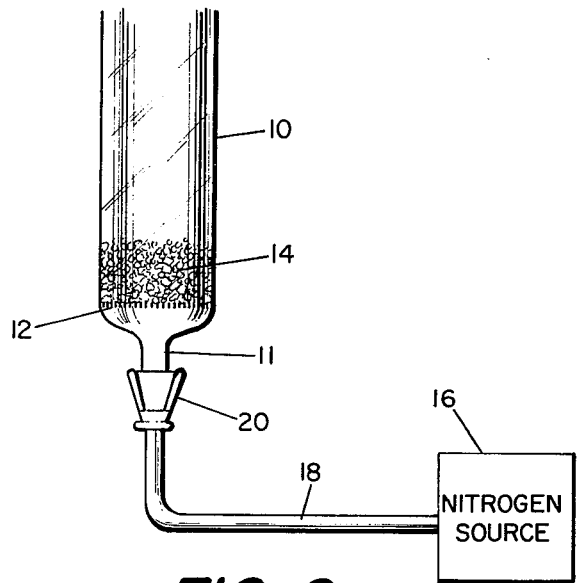
FIG. 2 is a representation of a fluidized bed apparatus that may be used to prepare a chromatographic support.

Although triglycidl glycerol was used in the example, any of the oxirane monomers listed in Table 3 may be used. It will be shown later that catalysts other than $BF_3$ may also be used. The most critical part of the process is to establish a thin surface layer of oxirane monomer before polymerization that will not fill the pores of porous supports. This is accomplished by either slurry (Howard Purnell, "Gas Chromatography", Wiley, New York, 1962, p. 240) or filtration (E. C. Horning, E. A. Moscatelli, and C. C. Sweeley, Chem. Ind. [London], 1959, 751) coating of the oxirane monomer on supports from a volatile solvent such as diethyl ether or acetone followed by fluidized drying [R. F. Kruppa, R. S. Henly, and P. L. Smead, Anal. Chem. 39, 851 (1967)]. As the volatile solvent evaporates in the fluidized drying apparatus, a film of oxirane monomer is deposited on the surface of the support. Numerous experiments with gas chromatographic packings have indicated that the liquid films also extend into the pores of porous supports. FIG. 1 shows an example of this ratus (shown in FIG. 2) as the coated packing material is being tumbled in a stream of nitrogen. Tumbling of the support during polymerization with a gaseous catalyst leaves the surface film of oxirane intact while preventing the aggregation of support particles.

Stationary phase ($P_s$) groups, i.e., ion exchangers and hydrophobic groups, are introduced into the polymer matrix in 3 ways; 1) copolymerization, 2) termination, and 3) grafting. In the copolymerization method, the unbound stationary phase or a derivative of ($P_s$) contains an oxirane functional group and may be copolymerized into the expoxy polymer matrix. The oxirane containing stationary phase has the general formula

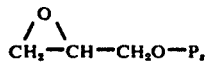

and is incorporated into polymers as indicated in reaction 5.

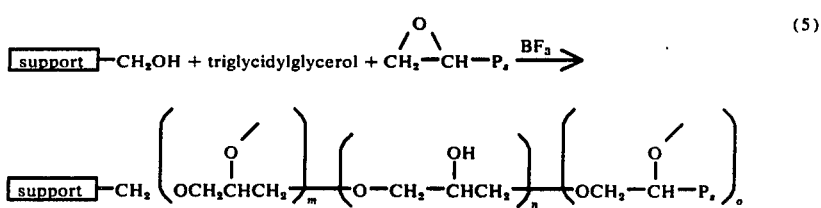

(5)

A listing of commercially available oxirane-$P_s$ monomers is shown in Table IV, as follows:

TABLE IV

| Name | Glycidyl-$P_s$ Monomers Formula |
|---|---|
| Methylglycidyl ether | $CH_2\!\!-\!\!\overset{\displaystyle O}{\overset{\displaystyle /\ \backslash}{CHCH_2OCH_3}}$ |
| Ethylglycidyl ether | $CH_2\!\!-\!\!\overset{\displaystyle O}{\overset{\displaystyle /\ \backslash}{CHCH_2OCH_2CH_3}}$ |
| Propylglycidyl ether | $CH_2\!\!-\!\!\overset{\displaystyle O}{\overset{\displaystyle /\ \backslash}{CH_2CH_2OCH_2CH_2CH_3}}$ |
| Hexylglycidyl ether | $CH_2\!\!-\!\!\overset{\displaystyle O}{\overset{\displaystyle /\ \backslash}{CHCH_2O(CH_2)_5CH_3}}$ |
| Tetradecylglycidyl ether | $CH_2\!\!-\!\!\overset{\displaystyle O}{\overset{\displaystyle /\ \backslash}{CH\!-\!CH_2O(CH_2)_{13}CH_3}}$ |
| Phenylglycidyl ether | $CH_2\!\!-\!\!\overset{\displaystyle O}{\overset{\displaystyle /\ \backslash}{CHCH_2O\!-\!\phi}}$ |
| p-Nitrophenylglycidyl ether | $CH_2\!\!-\!\!\overset{\displaystyle O}{\overset{\displaystyle /\ \backslash}{CHCH_2O\!-\!\phi\!-\!NO_2}}$ |

Copolymerization is accomplished in a fluidized bed with $BF_3$ catalysis in all cases. Equimolar ratios of oxirane monomer and stationary phase monomer were used.

Stationary phases ($P_s$) that contain a nucleophilic functional group may also be added to oxirane monomers during the course of polymerization as indicated in reaction 6. The group X- represents

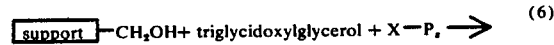

(6)

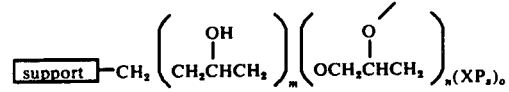

the nucleophile on the stationary phase before bonding. Since the addition of a nucleophile to the oxirane in this case essentially terminates its participation in further crosslinking reactions, this type of $P_s$ bonding is called "termination addition". Catalysts necessary for this type of reaction vary with $P_s$ and will be outlined more specifically below.

Grafting stationary phases ($P_s$) to preformed epoxy matrices may be achieved in several ways. In the first of these, an oxirane containing stationary phase

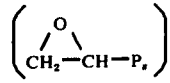

is added to the hydroxyl groups in the polymer matrix as shown in reaction 7.

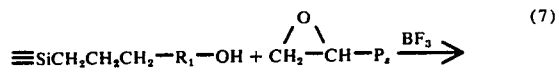 (7)

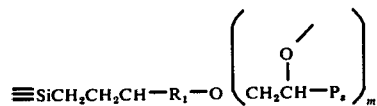

The bonding may be carried out in a manner identical to reaction 5. The basic difference here will be in the structure of the products. Since

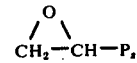

contains a single oxirane, a large amount of the polymer formation will be linear instead of cross linked.

Grafting may also be achieved by nucleophilic displacement of a leaving group Y (such as Cl, Br, or tosylate, for example) in the stationary phase ($P_s$) according to reaction 8.

 (8)

Detailed conditions of this reaction will be outlined below.

Inorganic supports that have a stationary phase bonded to the surface by one of the above procedures may be used to separate biological macromolecules in several ways. When the difference in the partition coefficients of two compounds is large, they may be separated in a "batch process". The bonded phase support is added to a solution of the mixture and the component(s) with large partition coefficients are bound. Filtration or centrifugation completes the resolution of components yielding a supernatant containing components with small partition coefficients.

When the differences in the partition coefficients of compounds are smaller, the above bonded phase supports must be packed into a column and used in a chromatographic process for the resolution of compounds. These bonded phase packings are ideal for pH gradient, ionic strength gradient, temperature, and flow programming. The rigidity of the inorganic matrix and the stability of the bonded phases permits the elution and regeneration of columns over a wide range of conditions without column degradation.

EXAMPLE I

Preparation of "GOX/CPG" Support

Ten grams of 74—128 $\mu$ (250A) controlled porosity glass (CPG) was treated with 100 ml of 6 N HCl at room temperature for 24 hrs. The support was then filtered, washed to neutrality with water, washed with acetone, and dried in vaccuo. Reaction 1 above describes the preparation of this support. The acid treated CPG was added to 1 liter round bottom flask and treated at 90° C for 30 min with 100 ml of a 5% aqueous solution of glycidoxypropyltrimethoxysilane (GOX) adjusted to pH 5.8. Gentle swirling of the flask every 5 min was used to mix the reactants. After completion of the reaction the support was filtered, washed with water and acetone, and dried in vaccuo. Elemental analysis of the resulting GOX support showed 1.2% carbon and 0.4% hydrogen. The "GOX/CPG" support is taught and claimed in U.S. Pat. No. 3,983,299 referred to hereinbefore.

EXAMPLE II

Preparation of "DEA/CPG" Support

Ten grams of 74-128 μ (250A) GOX/CPG support prepared according to Example I was added to a 500 ml round bottom flask fitted with a reflux condenser and tested at 50° C for 24 hrs with a solution containing 10% diethylamine (DEA) in dimethylformamide. After filtration, washing with acetone and ether, and vaccum drying the support had a hemoglobin ion exchange capacity of 40 mg/CC of support. This support was prepared according to reaction 2 in which the secondary amine is the nucleophile and the bonded phase has the general formula

$\equiv SiCH_2CH_2CH_2OCH_2CHOHCH_2N(CH\ CH_3)_2$.

Figure 4:
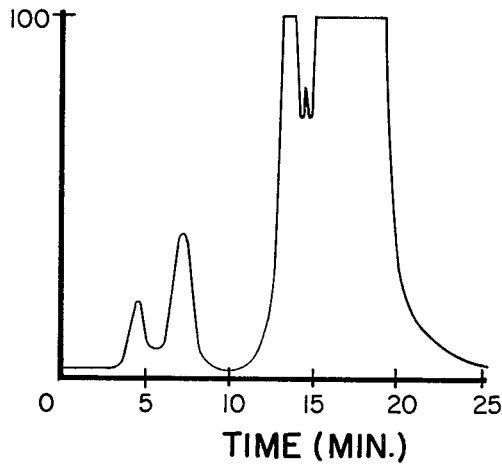
FIGS. 4 through 10 are elution curves showing achieved results.

The use of this support in the preparative resolution of goat serum proteins is shown in FIG. 4. Resolution is achieved in ½ to ¼ the time required with conventional carbohydrate anion exchange columns.

EXAMPLE III

Preparation of "DEAE/CPG" Supports

Figure 5:
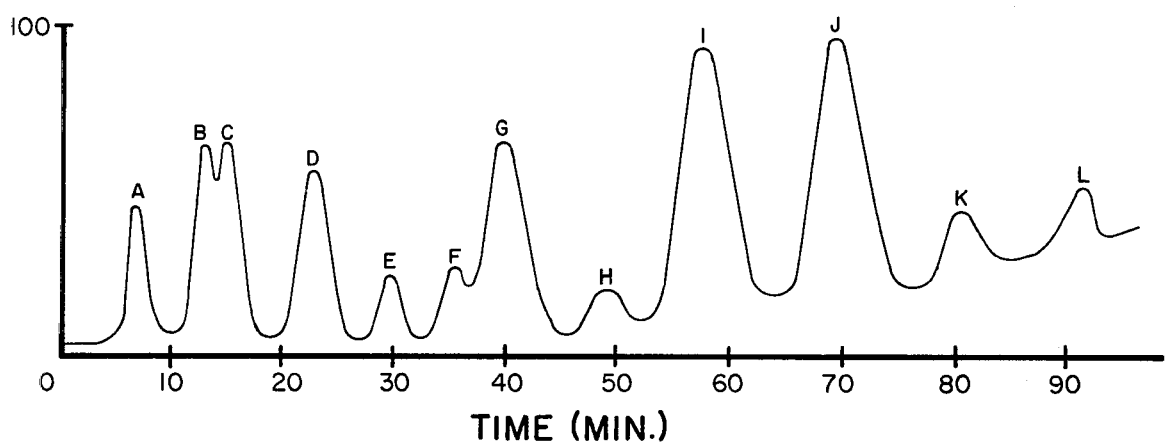

Ten grams of 74-128 μ (250A) GOX/CPG support prepared according to Example I was added to a 500 ml round bottom flask and treated at 100° C for 18 hrs with a solution containing 10% diethylaminoethanol (DEAE) in dimethylformamide. After filtration, washing with acetone and ether, and drying in vaccuo, this support had a hemoglobin ion exchange capacity of 34 mg/CC of support. Preparation of this support is according to reaction 2 in which the nucleophile is the alcohol portion of DEAE and the catalyst is the tertiary amine portion of the same molecule. This bonded phase has the structure $\equiv SiCH_2CH_2CH_2OCH_2CHOHCH_2OCH_2CH_2N(CH_2CH_3)_2$. The use of this weak anion exchange support in the high speed gradient elution analysis of horse serum is shown in FIG. 5. Resolution appears to be comparable to DEAE cellulose while the speed of analysis is 10 times that of the carbohydrate column.

EXAMPLE IV

Preparation of "SCX (Strong Cation Exchanger)/CPG" Supports

Ten grams of 74-128 μ (250A) GOX/CPG prepared according to Example I is added to an Erlenmeyer flask and treated at room temperature for 12 hrs with 100 ml of 1 M NaHSO₃ adjusted to pH 7. After filtration, washing with water, and air drying, the hemoglobin ion exchange capacity was 39 mg/CC of support. Preparation of this support fits reaction 2. The structure of the bonded phase is $\equiv SiCH_2CH_2CH_2OCH_2CHOHCH_2SO_3H$.

EXAMPLE V

Preparation of "PEG/CPG" Supports

Figure 6:
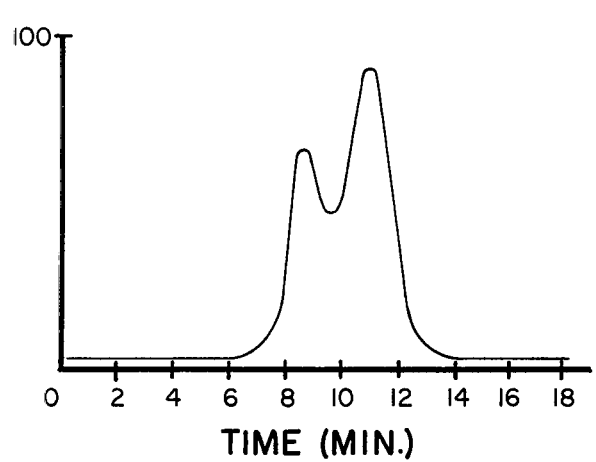

Ten grams of 74-128 μ (250A) GOX/CPG prepared according to Example I is added to a 500 ml Erlenmeyer flask containing 10 g of polyethylene glycol (PEG) 400 dissolved in 100 ml of dioxane. Boron triflouride-etherate (50% BF₃) is added dropwise to PEG-CPG suspension until a final concentration of 0.5% BF₃·Et₂O is reached. The reaction is complete in 4 hr at 25° C after which the solution is filtered, the support washed with acetone, and the PEG/CPG dried in vaccuo. Again the reaction proceeds according to reaction 2 with the alcohol functional groups of PEG serving as the nucleophile which BF₃·Et₂O is the catalyst. The formula of the bonded phase is $\equiv SiCH_2CH_2CH_2OCH_2CHOHCH_2(OCH_2CH_2)_{90}OH$. The use of this support in the resolution of commercial pancreatin is shown in FIG. 6.

EXAMPLE VI

Preparation of "PEI/CPG" Supports

Figure 7:
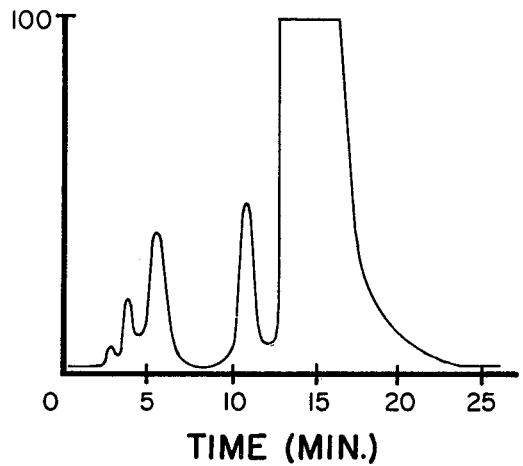

Ten grams of 37-74 μ (250A) GOX/CPG prepared according to Example I were added to a 250 ml round bottom flask and treated at 25° C for 18 hrs with 100 ml of dimethylformamide containing 10 g of polyethyleneimine (PEI) 200. After filtration, washing with water and acetone, and air drying, the support had a hemoglobin ion exchange capacity of 76 mg/CC of support. The use of this support in the resolution of human serum proteins is seen in FIG. 7.

EXAMPLE VII

Preparation of "Epoxy Polymer/CPG" Support

Ten grams of 74-128 μ (500 A pore diameter) glycerolpropylsilyl bonded CPG prepared according to the procedure outlined in U.S. Pat. No. 3,983,299 were added to a 2 inches × 36 inches glass chromatography column 10 (see FIG. 2) fitted with a 10 μ glass frit 12 above a narrowed portion 11. A nitrogen gas cylinder 16 was connected through passage 18 to the 24/40 joint 20 on the bottom of the column and the column support bed fluidized with a reverse flow of nitrogen. Fifty ml of diethyl ether containing 500 mg of diglycidylethylene glycol was added to the support and nitrogen flow continued until all of the ether had evaporated and the diglycidylethylene glycol coated support 14 was again tumbling freely in a fluidized bed. The nitrogen flow was temporarily interrupted and a 250 ml double necked (24/40) round bottom flask containing 25 ml of BF₃· etherate fitted on the bottom of the column. Connecting the nitrogen stream to the second joint of this flask again fluidized the support bed in addition to sweeping BF₃·etherate vapor into the fluidized bed. Polymerization of the oxirane monomer was completed in 15 min at 25° C. This bonded phase has the general formula

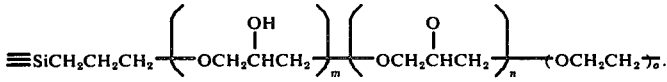

$$\equiv SiCH_2CH_2CH_2 {-}{\left(-OCH_2\underset{\underset{OH}{|}}{CH}CH_2-\right)}_m {\left(-OCH_2\underset{\underset{O}{|}}{CH}CH_2-\right)}_n {-(OCH_2CH_2)_{\overline{o}}}.$$

Figure 8:
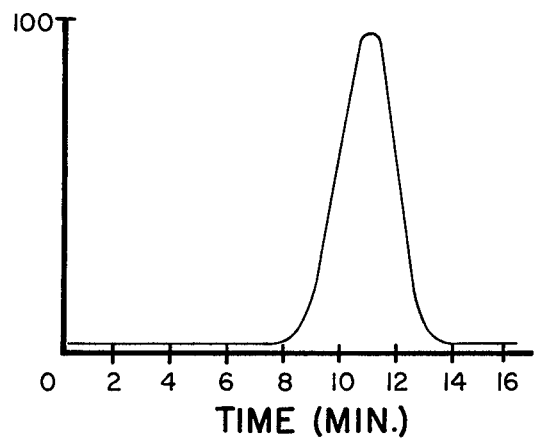

FIG. 8 shows non resolution of commercial trypsin when using this support.

Analysis seen later in Example X shows that this commercial trypsin sample contains many components. The inability of this "Epoxy Polymer/CPG" support to resolve the mixture indicates that the covalently bonded polymer is not functioning as a stationary phase for the separation of proteins, but is functioning as an inert matrix.

EXAMPLE VIII

Preparation of "CM (Carboxymethyl) Epoxy Polymer/CPG" Support

Ten grams of 74–128 μ (500 A pore diameter) glycerolpropylsilyl bonded CPG were prepared according to the procedure outlined in U.S. Pat. No. 3,983,299 and added to the fluidized bed apparatus described in Example VII. Fifty ml of diethylether containing 250 mg of diglycidylethylene glycol and 250 ml of allylglycidyl ether was added to the fluidizing apparatus and the ether evaporated to leave a film of the oxirane monomers on the support. Copolymerization was achieved in 15 min at 25° C by adding 25 ml of BF. etherate to the 250 ml flask on the fluidizer and sweeping BF· etherate vapors through the fluidized support bed. After purging with $N_2$, the diglycidylethylene glycol-allylglycidyl ether copolymer support was removed from the fluidizer and added to a 500 ml erlenmyer flask containing 200 ml of 8 mM sodium meta periodate, 2 mM potassium carbonate, and 0.134 mM potassium permanagante. Conversion of the ally group to the carboxymethyl cation exchanger was completed in 8 hrs at room temperature. Removal of oxidants by filtration was followed by a 500 ml wash with 1M sodium bisulfite and water washes to neutrality. A final wash with acetone and vaccum drying complete the preparation of the support. The general structure of this bonded phase is

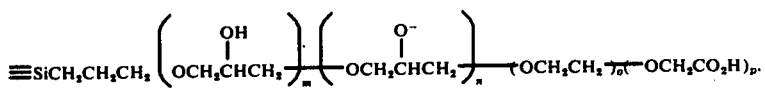

Figure 9:
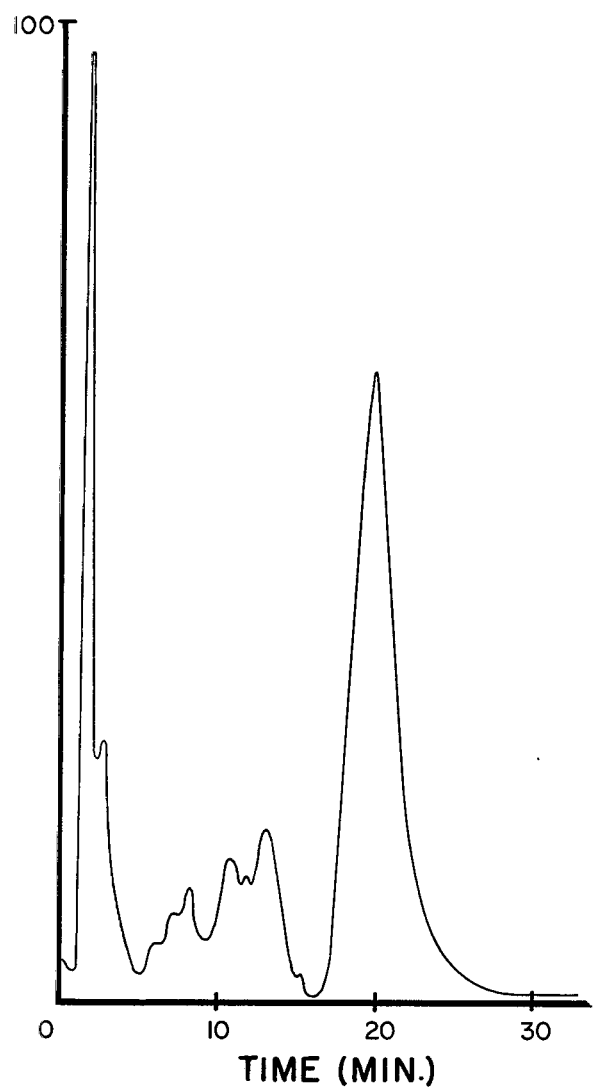

Hemoglobin ion exchange capacity was 20 mg/CC of support. The use of this CM support in the analysis of a commercial soybean trypsin inhibitor preparation is seen in FIG. 9.

EXAMPLE IX

Preparation of "SCX (Strong Cation Exchanger) Epoxy Polymer/CPG " Support

Ten grams of 74–128 μ (500 A) CPG bonded with diglycidylethylene glycol - allylglycidyl ether copolymer was prepared according to Example VIII. This support was added to a 500 ml erlenmyer flask and treated with 200 ml of 1M sodium bisulfite while oxygen was slowly bubbled through the solution for 4 hrs at 25° C. After filtration and water washing, the support was washed with acetone and air dried. The general formula representing the bonded phase is

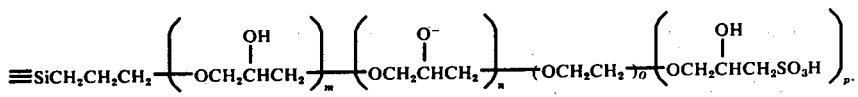

This support was found to have a hemoglobin ion exchange capacity of 20 mg/CC of support.

EXAMPLE X

Preparation of "DEAE Epoxy Polymer/CPG" Support

Ten grams of 74–128 μ (250 A) glycerolpropylsilyl bonded CPG prepared according to U.S. Pat. No. 3,983,299 was added to a 250 ml erlenmyer flask and treated for 18 hrs at 90° C with 100 ml of a solution containing 10% triglycidylglycerol, 40% diethylaminoethanol, and 50% dimethylformamide (v/v/v). After the support was separated by filtration, it was washed sequencially with dimethylformamide and acetone and then dried in vaccuo. The general formula for the bonded phase on this support is

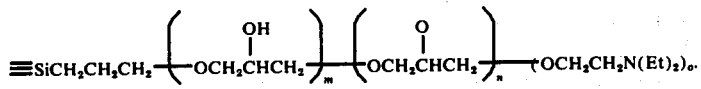

Figure 10:
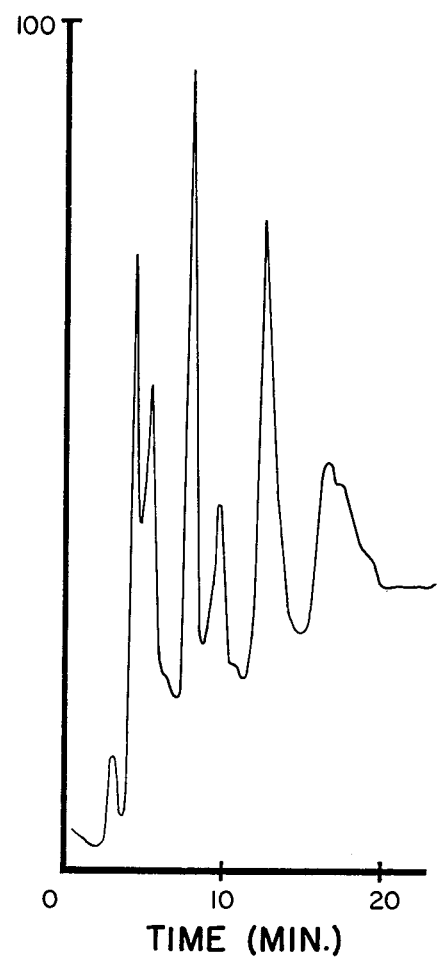

Ion exchange capacity of this support with hemoglobin is 76 mg/CC. The use of this support in the resolution of commercial trypsin is shown in FIG. 10.

Figure 3:
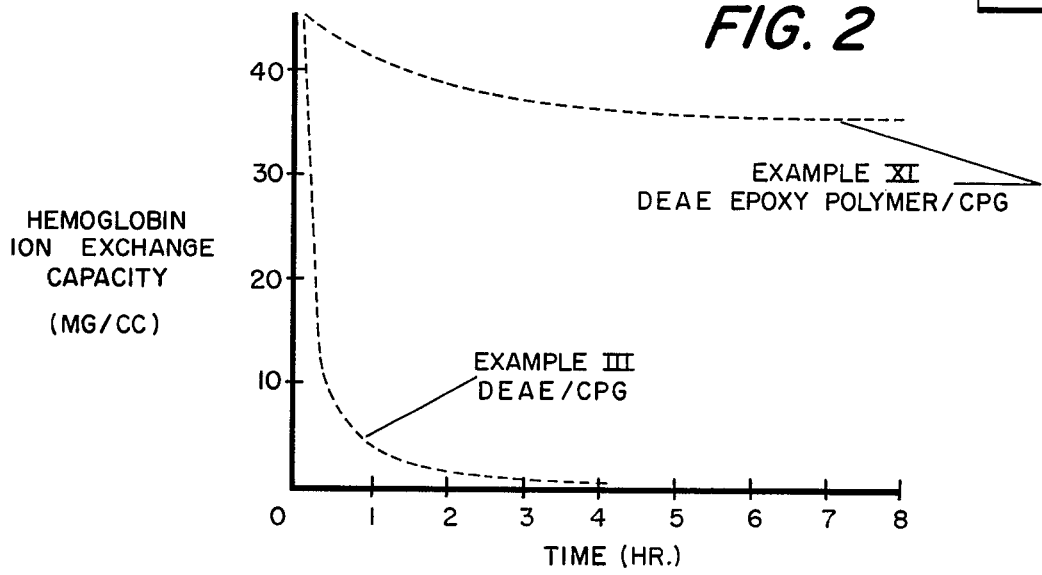
FIG. 3 is a graph showing stability of two anion exchange supports.

FIG. 3 shows the stability of the anion exchange supports of Examples III and X in a column that had 0.4 M sodium phosphate (pH 8.0) pumped through for 8 hrs at 100° C. The decrease in hemoglobin ion exchange capacity on these supports indicates that the stationary base ($P_s$) is eluting from the support. It is obvious that the polymer gives much greater stability to the support. The chromatographic properties of these two column supports are identical due to the same $P_s$.

EXAMPLE XI

Preparation of "QAE (Quaternary Anion Exchanger) Epoxy Polymer/CPG" Support

Ten grams of 74–128 (250 A) "DEAE Epoxy Polymer/ CPG" prepared according to Example X was added to a 250 ml round bottom flask fitted with a reflux condenser and treated for 12 hrs at reflux temperature with 10 g of methyl iodide in 100 ml of methanol. After completion of the reaction, the methanolic solution was removed by filtration and the support washed with acetone before drying in vaccuo. The general formula for the bonded phases in this support is

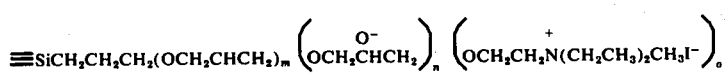

This support has a hemoglobin ion exchange capacity of 76 mg/CC of support.

EXAMPLE XII-XV

Preparation of "Hydrophobic Expoxy Polymer/CPG" Supports

These hydrophobic supports were prepared by the copolymerization of two epoxy monomers in the fluidized bed apparatus described above. The procedure is essentially identical to that for the preparation of the diglycidylethylene glycol allylglycidyl ether copolymer support in Example VIII. The supports and monomers used in the preparation of hydrophobic epoxy resin coatings are outline in Table V. Loadings and applications for these supports are also given in this Table. Table V is as follows:

TABLE V

The Preparation and Application of Hydrophobic Coatings

| Example | Support | Monomers |
|---|---|---|
| XII | 74–128 μ (250Å) glycerolpropyl-silyl/CPG | a. Diglycidyl-ethylene glycol<br>b. Glycidylpropyl ether |
| XIII | 74–128 μ (250Å) glycerolpropyl-silyl/CPG | a. Diglycidyl-ethylene glycol<br>b. Glycidyl-phenyl ether |
| XIV | 74–128μ (250Å) glycerolpropyl-silyl/CPG | a. Diglycidyl-ethylene glycol<br>b. Glycidyl nitro phenylether |
| XV | 74–128 μ (250Å) glycerolpropyl-sily/CPG | a. Diglycidyl-ethylene glycol<br>b. Glycidyl-tetradecyl ether |

| | Mg. monomer g. support | Percent Polymer by weight | Application |
|---|---|---|---|
| XII | a. 50<br>b. 50 | 10 | Hydrophobic Chromatography of proteins. |
| XIII | a. 50<br>b. 50 | 10 | Hydrophobic chromatography of proteins, peptides, and lipoprotein. Hydrophobic immobilization of enzymes. |
| XIV | a. 50<br>b. 50 | 10 | Hydrophobic immobilization of enzymes. Covalent immobilization of proteins. |
| XV | a. 50<br>b. 50 | 10 | Hydrophobic chromatography of peptides and steroids. Hydrophobic immobilization of enzymes. |

Elemental analysis of various chromatographic supports will be seen in Table VI, as follows:

Table VI

Microanalysis of Supports

| Element | Support | | | | |
|---|---|---|---|---|---|
| | DEA/CPG | DEAE/CPG | PEI/CPG | DEAE Epoxy/CPG | CM Epoxy/CPG |
| C% | 3.76 | 4.28 | 4.34 | 5.67 | 5.12 |
| H% | 0.66 | 0.70 | 0.67 | 0.92 | 0.87 |

From the foregoing, it can be appreciated that this invention provides improved chromatographic supports, as well as novel methods and apparatus for preparing the same.

What is claimed is:

1. A chromatographic support, comprising:
   an inorganic support matrix having a surface portion;
   a stationary phase for partitioning solutes, said stationary phase being a glycidyl ether selected from the group consisting of methanol, ethanol, propanol, hexanol, tetradecanol, phenol, and p-nitrophenol, a nucleophilic functional group, and a leaving group; and
   a silane coupling agent having one group for bonding to said surface portion of said support matrix and a second group for bonding to the stationary phase.

2. The chromatographic support of claim 1 wherein said stationary phase contains a nucleophilic functional group selected from the group consisting of OH, NH, $HSO_3$, and $HPO_4$.

3. The chromatographic support of claim 1 wherein said stationary phase contains a leaving group selected from the group consisting of Cl, Br, and tosylate.

* * * * *